(12) United States Patent
Bulletti

(10) Patent No.: US 10,016,522 B2
(45) Date of Patent: Jul. 10, 2018

(54) VAGINAL PREPARATION FOR THE DIAGNOSIS OF HUMAN FEMALE UTEROTUBAL PATENCY AND FUNCTION FOR THE PURPOSE OF FERTILIZATION OF GAMETES

(71) Applicant: Carlo Bulletti, Cattolica (IT)

(72) Inventor: Francesco Maria Bulletti, Cattolica (IT)

(73) Assignee: Carlo Bulletti, Cattolica (IT)

( * ) Notice: Subject to any disclaimer, the term of this patent is extended or adjusted under 35 U.S.C. 154(b) by 0 days.

(21) Appl. No.: 14/424,689

(22) PCT Filed: Aug. 27, 2013

(86) PCT No.: PCT/EP2013/067724
§ 371 (c)(1),
(2) Date: Feb. 27, 2015

(87) PCT Pub. No.: WO2014/033127
PCT Pub. Date: Mar. 6, 2014

(65) Prior Publication Data
US 2015/0231286 A1    Aug. 20, 2015

(30) Foreign Application Priority Data
Aug. 31, 2012  (IT) .............................. MI2012A1462

(51) Int. Cl.
  *A61K 51/12*  (2006.01)
  *A61K 49/00*  (2006.01)
  *A61K 49/18*  (2006.01)
  *A61K 49/10*  (2006.01)

(52) U.S. Cl.
  CPC ...... *A61K 51/1244* (2013.01); *A61K 49/0093* (2013.01); *A61K 49/10* (2013.01); *A61K 49/1827* (2013.01)

(58) Field of Classification Search
  CPC ................ A61K 49/0093; A61K 49/10; A61K 49/1827; A61K 51/1244
  USPC ....................................................... 424/1.33
  See application file for complete search history.

(56) References Cited

U.S. PATENT DOCUMENTS

2005/0181030 A1 * 8/2005 Mo ....................... A61K 9/0014
                                                        424/448
2009/0180964 A1 * 7/2009 Papineni ............... A61K 9/0073
                                                        424/9.3

FOREIGN PATENT DOCUMENTS

EP            1283060 A1 *  2/2003  ......... A61K 49/1815
WO        2007000283 A2     1/2007
WO    WO 2007000283 A2 *   1/2007  ......... A61K 51/1241

OTHER PUBLICATIONS

Venter, P F et al., "Migration of a Particulate Radioactive Tracer from the Vagina to the Peritoneal Cavity and Ovaries", Samj. South African Medical Journal, vol. 55, No. 23, Jun. 1, 1979, pp. 917-919.
McCalley, M G, et al., "Radionuclide Hysterosalpingography for Evaluation of Fallopian Tube Patency", Journal of Nuclear Medicine, vol. 26, No. 8, 1985, pp. 868-874.
McQueen D, et al., "Radionuclide Migration Through the Genital Tract in Infertile Women with Endometriosis", Human Reproduction, vol. 8, No. 11, 1993, pp. 1910-1914.
Cheong, Y.C., et al., "Evidence-Based Management of Tubal Disease and Infertility", Current Obstetrics and Gynaecology, Churchill Livinstone, Edinburgh, Great Britain, vol. 15, No. 5, Oct. 1, 2005, pp. 306-313.

* cited by examiner

*Primary Examiner* — Johann R Richter
*Assistant Examiner* — Courtney A Brown
(74) *Attorney, Agent, or Firm* — Pearne & Gordon LLP

(57) ABSTRACT

A vaginal preparation for the diagnosis of human female uterotubal patency and function, comprising particles having a nucleus absorbable by the tissues of the human body, and a coating for the nucleus which is dissolvable and non-absorbable by the tissues of the human body, inert and innocuous, the nucleus comprising at least one marker that can be released by the human body through an organic fluid, the coating being dissolvable and sensitive, for the purpose of the dissolution thereof, to time and/or changes in pH and/or temperature and/or another chemical/physical parameter along the route from the vaginal area to the tubal and pelvic area, the particles having a size, weight and ovoid shape corresponding approximately to those of spermatozoa.

9 Claims, No Drawings

VAGINAL PREPARATION FOR THE DIAGNOSIS OF HUMAN FEMALE UTEROTUBAL PATENCY AND FUNCTION FOR THE PURPOSE OF FERTILIZATION OF GAMETES

The present invention relates to a preparation and a kit and an apparatus for the diagnosis of human female uterotubal patency and the function of transporting gametes for the purpose of their fertilization.

When they turn to a physician to find solutions for their reproductive problems, sterile couples undergo a series of diagnostic tests aimed at defining the causes of their sterility.

A couple that have desired a pregnancy for over one year undergo an examination of seminal fluid, then analyses serving to establish a periodic ovulation and finally a test which establishes tubal patency (echo salpingoscopy, hysterosalpingography and laparoscopy). These tests are invasive and require the presence at least of a doctor, often of nursing staff and, in the case of laparoscopy, general anaesthesia along with ordinary surgical risks.

What is more, these examinations test tubal patency but not the contractile function of the uterus-tube-ovary unit whereby the spermatozoa and oocytes meet and one fertilizes the other. Physiologically, spermatozoa do not move by means of an autonomous force, but rather with a force produced by the aspirating contraction of the uterus.

Gametes (spermatozoa and oocytes) travel in the uterotubal tract by virtue of this contraction which, when well organized, promotes the transport of gametes for the purpose of making them meet and of the subsequent fertilization of the oocytes by the spermatozoa. An abnormal uterine contractility can render the fertilization process difficult, thus undermining the couple's fertility, i.e. causing infertility in couples who have uterine contractility that is insufficient for transporting the gametes.

The currently used techniques, known as hysterosalpingography or salpingography, rely on "non-physiological" methods (such as, for example, propulsion of a saline medium or radioopaque medium through the uterine cervix using a syringe) to evaluate the transit of a medium that is supposed to simulate the sperm while it passes through the uterine and tubal structures in order to meet the oocyte to be fertilized, usually in the outer third of the tube, and determine tubal patency with an ultrasound scanner (echo salpingography) or with X-rays (hysterosalpingography).

The technical task that the present invention sets itself is thus to realize a preparation and a kit for the diagnosis of human female uterotubal patency and function which enable the technical drawbacks of the prior art to be eliminated.

Within the scope of this technical task, one object of the invention is to realize a preparation and a kit for the diagnosis of human female uterotubal patency and function that is capable of simultaneously evaluating both the transport function of uterine and tubal muscles and their patency, without discrimination between one tube and both tubes.

Another object of the invention is to realize a preparation and a kit for diagnosing human female uterotubal patency and function in a manner that is painless and free of health risks and risks of pelvic infections.

Last but not least, it is an object of the invention to realize a preparation and a kit for the diagnosis of human female uterotubal patency and function that enable the test to be carried out autonomously in a home environment without requiring machinery, the assistance of doctors or nurses, or hospitalization.

The technical task, as well as these and other objects, according to the present invention, are achieved by realizing a vaginal preparation for the diagnosis of human female uterotubal patency and function, characterized in that it comprises particles having a nucleus absorbable by the tissues of the human body and a coating for the nucleus which is dissolvable, inert and innocuous for the tissues of the human body, said nucleus comprising at least one marker that can be released by the human body through an organic fluid, said coating being dissolvable and sensitive, to enable its dissolution, to time and/or changes in pH and/or temperature and/or another chemical/physical parameter along the route from the vaginal area to the tubal and pelvic area, said particles having a size, weight and ovoid shape corresponding approximately to those of human spermatozoa.

Advantageously, the particles are suspended in a dispersion medium which simulates human seminal fluid in terms of pH and density and comprises prostaglandin f2alpha and prostaglandin E at the concentrations and ratios physiologically present in human seminal fluid.

The preparation is thus made up of a functional unit of particles and a dispersion medium that proactively determine an adequate transport of the particles at the anatomic sites physiologically responsible for in vivo fertilization, thereby revealing an adequate transport of the particles versus an inadequate transport and a condition of potential fertility versus another of potential infertility.

In fact, according to the present invention the transit of the medium which simulates sperm takes place "physiologically" thanks to a sort of spontaneous propulsive "peristaltic-like" contraction of the uterine and tubal muscles, and certainly not as result of pushes by syringes, as occurs in the prior art. A propulsive contractility can be adequate (in a fertile woman) or inadequate (in a sterile woman) irrespective of whether the tubes are patent or not.

The preparation according to the invention can be used in two types of tests with two different substances characterizing the same principle: that of a physiological transport of spermatozoa from the vagina to the outer third of the tube, where the spermatozoa themselves fertilize the oocytes that have descended there from the ovary (a transport that determines the couple's possibility of procreating depending on whether it is adequate or inadequate).

Both tests can be performed autonomously by women with problems of sterility: in a home environment with the aid of an outside laboratory equipped with a mass spectrometer to which the specimens may be sent for a reading of the first type of test (which here we shall call Test Substance 1); without the aid of instruments or machinery for its analysis and with results that can be read at home in the case of second type of test (which here we shall call Test Substance 2).

Both types of test are to be considered like a functional unit exploiting the synergy between the particles and dispersion medium, because the latter contains not only passive support elements, but also active elements that induce transport by inducing propulsive muscular contraction (the prostaglandins, abbreviated as PGs).

The dose of the preparation used for the diagnosis preferably comprises:
approximately 250 million micro particles (core+coating).
approximately 5 ml of dispersion medium In the dose of the preparation, the particles are preferably suspended in the dispersion medium in a ratio of about 5:95.

The particles preferably have a length in the range of 10-60 microns.

As noted, the dispersion medium includes prostaglandins (PGf2alpha and PGE) in concentrations and in a ratio between the different PGs which are physiologically present in human seminal fluid. The inclusion of PGs in the dispersion medium has the purpose of determining the cervical-uterine contraction available for transporting the test substance from the vagina, where the pH is around 5, to the outer third of the tube, where it is around 7, in a period of time of 30 minutes-5 hours.

The test must strictly be performed in a pre-ovulation phase (days of an average menstrual cycle, days 12-14 of the cycle), because in this phase, the spontaneous uterine contractility developed by the prostaglandins of the release medium are propulsive with a cervical-fundal direction in the population of fertile women.

The present invention also discloses a kit for the diagnosis of human female uterotubal patency and function, characterized in that it comprises at least one dose of the preparation.

The kit preferably also comprises a breath or organic fluid collector and a vaginal pH tester.

The kit preferably further comprises means for analyzing the organic fluid in order to detect the presence of the marker.

The preparation and kit are instruments capable of determining, in addition to tubal patency, whether the contractile function of this genital tract of the woman concerned is such as to enable the transport of gametes and their passage through the tubes, and thus the adequacy of the transport function indispensable for fertilization, without the assistance of doctors or nurses and without hospitalization.

In practical terms, with the preparation and kit according to the invention it is possible to verify the gamete transport function of the vagina-uterus-tube-ovaries unit and the correct anatomy of these structures in order to be able to determine their in vivo fertility or infertility and the consequent need for in vitro fertilization. Other features of the present invention are defined, moreover, in the subsequent claims.

Additional features and advantages of the invention will be more apparent from the following description of preferred, but non-exclusive examples of tests performed with the preparations according to the invention for the diagnosis of human female uterotubal patency and function.

As noted, the vaginal preparation for the diagnosis of human female uterotubal patency and function comprises: particles having a nucleus absorbable by the tissues of the human body and a coating for the nucleus which is dissolvable, inert and innocuous for the tissues of the human body; and a dispersion medium for the particles which simulates seminal plasma in terms of pH and density, contains other substances included among those present in seminal plasma and is supplemented with prostaglandin f2alpha and prostaglandin E in the same amount and ratio as in a normal ejaculate. The coating is dissolvable and sensitive, for the purpose of the dissolution thereof, to time and/or changes in pH and/or temperature and/or another chemical/physical parameter along the route from the vaginal area to the tubal and pelvic area. The particles have a size, weight and ovoid shape corresponding approximately to those of human spermatozoa.

The release medium can be in various forms, for example in the form of a solution, emulsion or gel or cream or oil, or a micronized or non-micronized tablet. But with the general constituent physicochemical characteristics of a seminal fluid.

The marker can be of various types; in particular, a radioactive marker of proven innocuousness or a colorimetric marker have shown to be especially effective.

Moreover, the nucleus may or may not have a removable vehicle to which the marker is bound.

If a vehicle is provided, it is preferably sensitive, to enable its removal, to a specific biochemical agent present at least in the tubal and pelvic area.

In the present invention, organic fluid means any gas or liquid that is released by the human body. By way of non-limiting example, organic fluids include breath exhaled from the lungs or urine.

The coating could be resorbable, but only when it is dissolved (under the pre-established conditions) and certainly in an inert manner, i.e. without any function either of determining or modifying functions. Experimental trials have shown that, once dissolved, the coating is substantially resorbed because the absorption capacity of the peritoneum is enormous; but this does not create any problem, since the coating is made of an inert, innocuous material. The coating is identified among the substances (usually polymers) capable of dissolving with changes in pH—here from 5 to >6.5—or at various times or else with changes in temperature. Examples of the usable coating forms are Eudragit S100, Eudragit L100 and Eudragit RS (1).

There are two different types of markers used for the diagnostic test, given both the same coating and proactive dispersion medium for contraction and support, which works together with the suspended particles as a functional unit. The two markers are Urea-13C and Riboflavin or Vitamin B12.

Urea-13C in an amount of 100-150 mg is included in a coating with pH and/or time dependent dissolution, from pH 5 to pH>6.5 and/or from 30 min to 5 hours. Riboflavin or Vitamin B12 is a vitamin that is excreted with urine and—when taken—imparts a bright colour to it (orange). Vitamin B12 has the almost exclusive property of being a water-soluble vitamin. The normal colour of urine, depending on its state of hydration, ranges from pale yellow to amber. The intake of large amounts vitamin B12 causes the colour of urine to turn a bright orange that is easily recognizable to the naked eye. The administration of vitamin B12 in water-soluble form—because it is retained in the coating—in the vagina and transported by a uterine contractility in the pelvis, where it dissolves due to the change in pH, releases the vitamin B12 which—given its solubility and absorbability, enters into circulation and is eliminated with urine, imparting a bright orange colour to it. This would not happen if the transport of vitamin B12 was not ensured by adequate uterine contractility or in the event of a lack of contraction or obstruction (blocked tubes or adhesions). In this case the coating would remain at a pH of 5 for a long period without dissolving and releasing the vitamin and without causing the colour of the urine to change, making the test negative. An intake of 2.4 micrograms per day (even much larger doses can be administered, because the vitamin is not absorbed and the excess portion is eliminated—precisely—with urine) is sufficient to determine a clearly visible colouring of urine. Conditions of severe infection or the simultaneous intake of other drugs at the time of the test or the use of large quantities of multivitamins are to be excluded.

The kit comprises means for analyzing the organic fluid, which can be, by way of non-limiting example, testers or stabilizers for analyses to be performed immediately on site or, alternatively, means for analyses to be performed remotely, such as, for example, by spectrometry.

Some example of diagnostic tests with preparations and kits according to the invention are shown below.

EXAMPLE 1

The nucleus comprises a radioactive marker bound to a vehicle.

The marker used consists in C-13, already used in gastroenterological tests for diagnosing malabsorption or helicobacter pylori syndromes.

The biodegradable vehicle used for C-13 is urea.

The presupposition, as is well known, is that both pH and temperature change in the tract made up of the vagina-uterus-tube-pelvic cavity, and that in a periovulatory follicular phase uterine contractility is physiologically cervical-fundal in order to transport spermatozoa from the vagina to the outer third of the tubes. This transport is made exploitable thanks to the enhancement of this function produced by the prostaglandins physiologically present in the seminal fluid deposited in the vagina and, in the diagnostic test, by the prostaglandins enriching the particle suspension/release medium of Test Substance 1 and Test Substance 2.

The diagnostic test is performed in the following manner.

Use is made of a kit comprising at least one dose of the preparation (with Test Substance 1 or 2), a breath collector (if Test Substance 1 is used) or a urine collector with an attached colorimetric indicator (in the case of Test Substance 2), a vaginal pH tester, and means for collecting and/or analyzing the breath exhaled from the lungs to detect the presence of C-13.

Initially, the subject to be tested by means of the pH tester, for example litmus paper, evaluates the degree of vaginal acidity. Only if this corresponds to the absence of vaginitis (which can be detected through changes in the acidity of the vaginal environment) will it be possible to proceed with the test.

The subject introduces the product into her vagina, strictly during the advanced follicular phase (between +12th and +14th day of the cycle), and waits for a time ranging from 5 minutes to 24 hours (according to the type of coating, the dissolution of which depends on time, pH, temperature or a combination of more than one of these factors).

If the genital tract is intact in terms of propulsive contractile function and tubal patency, the particles of the preparation will be pushed into the outer third of the tubes or into the pelvic cavity, where, as a result of dissolution, they will lose their coating, which will thus release the nucleus of C-13 and urea.

The nucleus without a protective coating will find the biochemical agent, in particular the enzyme called urease, which will hydrolytically split the urea into ammonia and carbon dioxide, thus finally releasing C-13 (in the case of Test Substance 1).

At this point, the C-13 is freely and rapidly absorbed by tissues, transported into pulmonary circulation and from here to the alveoli in order to be gradually exhaled.

The exhaled breath collected in the specific collector will be examined at this point with the means of analysis, in particular a spectrophotometer.

The presence of C-13 in the breath means that: the particles were properly carried from the vagina to the outer third of the tubes or into the pelvic cavity, as could occur with spermatozoa; the tube is open; the coating found conditions therein to be dissolved; and the radioactive marker was transported accordingly in the breath.

This test result indicates that the subject can seek a pregnancy by spontaneous in vivo fertilization or with the help of assisted conception techniques.

The absence of C-13 in the breath instead means that: the particles were not transported (either because of inadequate uterine contractions or tubal impatency) from the vagina to the outer third of the tubes or into the pelvic cavity where there exist conditions for dissolving the coating; and there exists an obstacle to the union and fertilization of gametes.

This test result indicates that the subject can seek a pregnancy by in vitro fertilization.

EXAMPLE 2

The nucleus comprises a colorimetric marker (Test Substance 2), in particular a vital dye or a substance such as vitamin B12 or Methylene Blue or another inert, innocuous colouring agent capable of taking on a different colour as it passes through environments (for example urine) with different physicochemical properties or of releasing colour when removed from the coating which is dissolvable with changes in pH or temperature.

Use is made of a kit comprising at least one dose of the preparation, a urine collector, a vaginal pH tester, and means of colorimetric urine analysis for detecting the presence of the colorimetric marker.

Initially, the subject to be tested by means of the pH tester, for example litmus paper, evaluates the degree of vaginal acidity. Only if this corresponds to the absence of vaginitis will it be possible to proceed with the test.

The subject introduces the product into her vagina, strictly during the advanced follicular phase (between +12th and +14th day of the cycle), and waits for a time ranging from 5 minutes to 24 hours (according to the type of coating, the dissolution of which depends on time, pH, temperature or a combination of more than one of these factors)

If the genital tract is intact in terms of propulsive contractile function and tubal patency, the particles of the preparation will be pushed into the outer third of the tubes or into the pelvic cavity, where, as a result of dissolution, they will lose their coating, which will thus release the nucleus consisting of the colorimetric marker, which is first absorbed by body tissues and then expelled with urine.

The urine is collected in the specific container and examined using the means of analysis, which can be simply a label applied on the urine container and providing a visual indication of the meaning of the colour found in the collected urine.

The presence of the colorimetric marker in the urine means that: the particles were properly carried from the vagina into the outer third of the tubes or into the pelvic cavity, as could occur with spermatozoa; the tube is open; the coating found conditions therein to be dissolved (change in pH or temperature); and the coloured marker was transported accordingly in the urine.

This test result indicates that the subject can seek a pregnancy by spontaneous in vivo fertilization or with the help of assisted conception techniques (for example IUI—intrauterine insemination).

The absence of the colorimetric marker in the urine instead means that: the particles were not transported (either because of inadequate uterine contractions or tubal impatency) from the vagina to the outer third of the tubes or into the pelvic cavity where there exist conditions for dissolving the coating; and there exists an obstacle, which is manifested here with the absence of the colouring agent in the urine and in the woman's biology in that no union of gametes or fertilization takes place.

This test result indicates that the subject can seek a pregnancy by in vitro fertilization.

Advantageously, the test exploits the function of uterine contractility, rather than relying on morphology alone (open and closed tubes).

The test has the ability to diagnose the patency and function of the uterotubal unit, can be performed autonomously in a home environment without the need for hospitalization or the assistance of a doctor or nurse, and is painless and extremely easy to use.

The preparation and kit for the diagnosis of female uterotubal patency and function thus conceived are susceptible of numerous modifications and variants, all falling within the scope of the inventive concept; moreover, all the details may be replaced with technically equivalent elements.

The invention claimed is:

1. A vaginal preparation for the diagnosis of human female uterotubal patency and function, characterized in that it comprises particles and a dispersion medium wherein:
   the particles have: (1) size of 10-60 microns, weight and ovoid shape corresponding approximately to those of human spermatozoa; (2) a nucleus absorbable by the tissues of the human body and comprising at least one marker that can be released by the human body through an organic fluid; and (3) a coating which is dissolvable at pH>6.5, inert and innocuous for the tissues of the human body; and
   the dispersion medium simulates the human seminal fluid in terms of pH and density and comprises a combination of prostaglandin (PG) f2alpha and prostaglandin E at the concentrations and ratios physiologically present in human seminal fluid, said prostaglandins being able to determine cervical-uterine contraction needed for transporting the particles from the vagina to the outer third of the tube in ½-5 hour(s).

2. The vaginal preparation according to claim 1, characterized in that said nucleus has a removable vehicle to which said marker is bound.

3. The vaginal preparation according to claim 1, characterized in that said marker is radioactive.

4. The vaginal preparation according to claim 2, wherein said marker is C-13 and said vehicle is urea and can be removed by hydrolytic splitting promoted by said biochemical agent, consisting of urease.

5. The vaginal preparation according to claim 1, characterized in that said marker is colorimetric.

6. A kit for diagnosing human female uterotubal patency and function, characterized in that it comprises:
   at least one dose of a preparation according to claim 1, wherein said preparation comprises approximately 250 million of the particles suspended in the dispersion medium.

7. The vaginal preparation according to claim 1, wherein a ratio between the particles and the dispersion medium is about 5:95.

8. The kit according to claim 6, characterized in that it further comprises a breath or organic fluid collector and a vaginal pH tester.

9. The vaginal preparation according to claim 1, characterized in that said marker is selected from: Urea-13C, Riboflavin and Vitamin B12.

* * * * *